US010154984B2

(12) United States Patent
Chen et al.

(10) Patent No.: US 10,154,984 B2
(45) Date of Patent: *Dec. 18, 2018

(54) DIACEREIN OR RHEIN TOPICAL FORMULATIONS AND USES THEREOF

(71) Applicant: TWi Biotechnology, Inc., Taipei (TW)

(72) Inventors: Chih-Kuang Chen, Taipei (TW); Jing-Yi Lee, Taipei (TW); Wei-Shu Lu, Taipei (TW); Carl Oscar Brown, III, San Diego, CA (US)

(73) Assignee: TWi Biotechnology, Inc. (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/658,725

(22) Filed: Jul. 25, 2017

(65) Prior Publication Data
US 2018/0021290 A1 Jan. 25, 2018

Related U.S. Application Data

(63) Continuation-in-part of application No. 15/198,728, filed on Jun. 30, 2016, now Pat. No. 9,744,131.
(Continued)

(51) Int. Cl.
| A61K 31/325 | (2006.01) |
| A61K 31/235 | (2006.01) |
| A61K 9/14 | (2006.01) |
| A61K 9/06 | (2006.01) |
| A61K 9/00 | (2006.01) |
| A61K 31/192 | (2006.01) |
| A61K 31/225 | (2006.01) |
| A61K 47/10 | (2017.01) |
| A61K 47/12 | (2006.01) |
| A61K 47/14 | (2017.01) |
| A61K 47/18 | (2017.01) |

(Continued)

(52) U.S. Cl.
CPC .......... *A61K 31/235* (2013.01); *A61K 9/0014* (2013.01); *A61K 9/06* (2013.01); *A61K 9/145* (2013.01); *A61K 31/192* (2013.01); *A61K 31/225* (2013.01); *A61K 47/10* (2013.01); *A61K 47/12* (2013.01); *A61K 47/14* (2013.01); *A61K 47/183* (2013.01); *A61K 47/26* (2013.01); *A61K 47/32* (2013.01); *A61K 47/44* (2013.01)

(58) Field of Classification Search
CPC .. A61K 31/235; A61K 31/225; A61K 31/192; A61K 9/0014; A61K 9/145; A61K 9/06; A61K 47/44; A61K 47/32; A61K 47/26; A61K 47/183; A61K 47/14; A61K 47/12; A61K 47/10
See application file for complete search history.

(56) References Cited

U.S. PATENT DOCUMENTS

| 2010/0285114 | A1* | 11/2010 | Dabre | A61K 9/1635 424/451 |
| 2012/0301527 | A1* | 11/2012 | Friedman | A61K 8/06 424/401 |
| 2013/0156857 | A1* | 6/2013 | Gao | A61K 9/146 424/490 |

FOREIGN PATENT DOCUMENTS

| WO | WO 2006/029189 A2 * | 3/2006 |
| WO | WO 2009/133430 A1 * | 11/2009 |

* cited by examiner

Primary Examiner — Aradhana Sasan
Assistant Examiner — Quanglong N Truong
(74) Attorney, Agent, or Firm — Wood, Phillips, Katz, Clark & Mortimer

(57) ABSTRACT

A topical pharmaceutical composition containing diacerein and/or its analogs is provided. Also provided is a method for treating various diseases using this topical pharmaceutical composition.

12 Claims, 4 Drawing Sheets

Related U.S. Application Data

(60) Provisional application No. 62/187,743, filed on Jul. 1, 2015.

(51) Int. Cl.
*A61K 47/26* (2006.01)
*A61K 47/32* (2006.01)
*A61K 47/44* (2017.01)

DIACEREIN OR RHEIN TOPICAL FORMULATIONS AND USES THEREOF

BACKGROUND OF THE INVENTION

Field of the Invention

The present invention relates to a topical pharmaceutical composition containing diacerein and/or its analogs, and also relates to uses of this topical pharmaceutical composition in treatment of various diseases or conditions.

Descriptions of the Related Art

Chemically, rhein is 9, 10-dihydro-4, 5-dihydroxy-9, 10-dioxo-2-anthracene carboxylic acid having a structure of Formula (I), and one of its prodrugs, diacerein, is 4, 5-bis (acetyloxy) 9, 10-dihydro-4, 5-dihydroxy-9, 10-dioxo-2-anthracenecarboxylic acid having a structure of Formula (II). Diacerein is entirely converted into rhein before reaching the systemic circulation, and exerts its physiological function in form of rhein within the body.

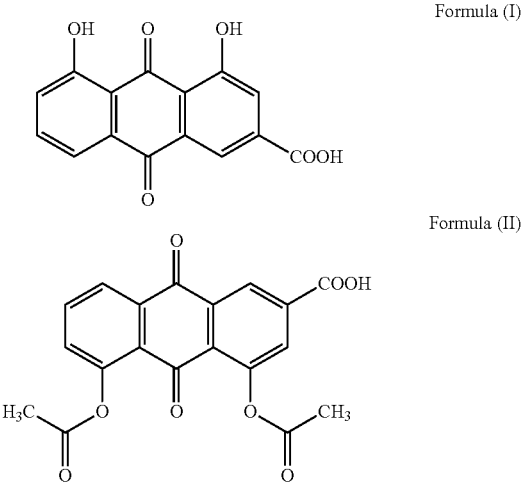

Diacerein is an anti-inflammatory agent widely used in the treatment of osteoarthritis, which has been demonstrated to inhibit interleukin-1 (IL-1) signaling. Presently, diacerein capsules are available in 50 mg strength and are marketed under various trade names in different countries, including Art 50®, Artrodar®, etc. As disclosed in U.S. Pat. Nos. 8,536,152 and 8,865,689, diacerein can be used as an adjunctive treatment for type II diabetes mellitus, and was also found to be effective in reducing blood uric acid levels and can accordingly be used for treating hyperuricemia or a metabolic disorder associated with hyperuricemia. In addition, it has been reported that diacerein has a potential effect in the treatment of epidermolysis bullosa (Wally et al., Orphanet Journal of Rare Diseases, 2013, vol. 8, issue 69).

Although diacerein can be administered by the oral route, it cannot be completely absorbed by the digestive tract, and the oral bioavailability of diacerein has been estimated to be approximately 40% to 60%. The incomplete absorption of diacerein may result in undesirable side effects such as diarrhea or soft stools. In vitro and in vivo studies have showed that non-absorbed diacerein is metabolized to rhein in the colon, which then induces a laxative effect.

Since such side effects may occur due to oral administration, non-oral diacerein compositions have been proposed to overcome these problems.

PCT International Application No. WO 2009/133430 discloses topical compositions containing diacerein or rhein, which can be in various forms, such as a lotion, cream, ointment, paste, gel, etc. However, these compositions are not intended for any specific disease, and thus one cannot know which form would be most suitable for a certain kind of disease to be treated from the context of this article.

Wally et al. disclosed a cream diacerein formulation for epidermolysis bullosa (Wally et al., Orphanet Journal of Rare Diseases, 2013, vol. 8, issue 69). However, it is unclear whether or how the properties of the formulation affect the treatment efficacy on epidermolysis bullosa from this article.

It appears that precise properties of diacerein formulations are very important for its treatment efficacy for different diseases.

Considering that the literature provides little information about the relationship between physicochemical properties of a diacerein/rhein topical formulation and its treatment effect, the present invention provides topical formulations adapted to different diseases accordingly.

SUMMARY OF THE INVENTION

This invention provides a topical composition comprising a therapeutically effective amount of a compound selected from the group consisting of diacerein, rhein, monoacetylrhein, and salts or esters or prodrugs thereof, and one or more pharmaceutically acceptable excipients, wherein the composition is in the form of ointment, cream, or gel, and at least about 90% by volume of the compound has a particle size of about 0.5 to 35 µm.

This invention also provides a topical composition comprising a therapeutically effective amount of a compound selected from the group consisting of diacerein, rhein, monoacetylrhein, and salts or esters or prodrugs thereof, and one or more pharmaceutically acceptable excipients, wherein the composition is in the form of gel, and at least about 90% by volume of the compound has a particle size of less than about 1 µm.

This invention also provides a method of treating inflammatory and/or hyperproliferative and pruritic skin diseases, and diseases with epithelial barrier dysfunction including aged skin and epidermolysis bullosa, comprising administering to a subject in need thereof an effective amount of the composition of the present invention.

This invention also provides a method of treating hyperuricemia, a metabolic disorder associated with hyperuricemia, osteoarthritis or type 2 diabetes mellitus, comprising administering to a subject in need thereof an effective amount of the composition of the present invention.

In some embodiments, the treatment methods of the invention specifically exclude administration of any other active agents to treat the diseases treatable by the compositions of the present invention. In some embodiments, however, the methods allow for administration of other active agents.

Preferably, the treatment methods of the invention result in effective treatment of the relevant disease in at least one treated subject, and preferably, in the substantial number of the treated subjects, and more preferably, in the majority of the treated subjects.

The detailed technology and preferred embodiments implemented for the subject invention are described in the following paragraphs accompanying the appended drawings for people skilled in this field to well appreciate the features of the claimed invention.

DETAILED DESCRIPTION OF THE INVENTION

Figure 1:
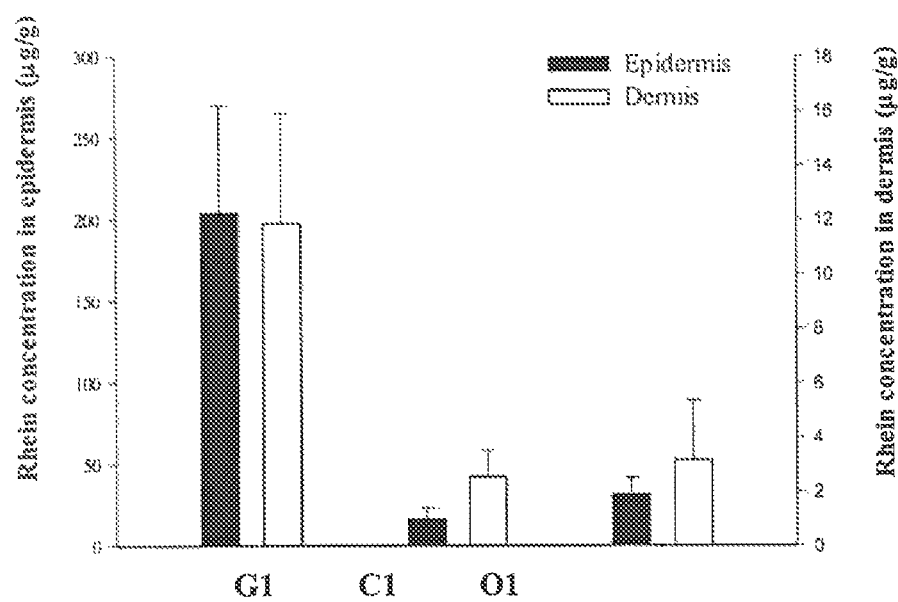
FIG. 1 is a statistical bar graph showing rhein concentrations in dermis and epidermis post 8 hours treatment with three tested diacerein formulations (G1, C1 and O1, n=4)

The term "therapeutically effective amount," as used herein, refers to an amount that alleviates or reduces one or more symptoms of a disease.

The term "diacerein or its analogs," as used herein, refers to diacerein, rhein, monoacetylrhein, or a pharmaceutically acceptable salt or ester or a prodrug thereof.

Unless otherwise stated herein, the terms "a (an)", "the" or the like used in this specification (especially in the Claims hereinafter) shall be understood to encompass both the singular form and the plural form.

As stated above, topical administration of diacerein may prevent undesired side effects of oral administration since it bypasses the gastrointestinal route which has tolerability limitations, and reduces the amount of diacerein entering into systemic circulation, as compared to oral administration. Besides, when diacerein is used to treat skin diseases, it is advantageous that diacerein may penetrate through the stratum corneum easily to reach the target site (e.g., dermis or epidermis, where skin disorders may occur). Meanwhile, it is also desired that diacerein is retained in the skin as long as possible to exert its function sufficiently. Therefore, a delicate balance needs to be achieved so as to, on the one hand, allow diacerein or rhein to penetrate into the target site quickly, but on the other hand, retain it in the target site for extended exposure.

The inventors of the present invention discovered that the form of a topical diacerein/rhein composition and/or the particle size of an active component contained therein play key roles in penetrability (or diffusivity) and the retention rate in the skin.

The present invention thus provides a topical diacerein/rhein pharmaceutical composition that is suitable for skin diseases and meets the above requirement. The topical pharmaceutical composition comprises a therapeutically effective amount of a compound selected from the group consisting of diacerein, rhein, monoacetylrhein, and salts or esters or prodrugs thereof, and one or more pharmaceutically acceptable excipients, wherein the composition is in the form of ointment, cream, or gel, and at least about 90% by volume of the compound has a particle size of about 0.5 to 35 μm, and more preferably, of about 14 to about 20 μm.

The particle size distribution in the context of this application is based on volume D values (i.e., Dv values, such as Dv10, Dv50 and Dv90), which are commonly used to represent a range of the particle sizes of a given sample.

Preferably, the composition is provided as an ointment or cream, and more preferably as an ointment. It was unexpectedly found that an ointment or cream formulation provides higher retention rate and longer retention time in the skin as compared to a gel formulation.

In one embodiment, at least about 90% by volume of the compound in the composition has a particle size of about 1 to about 15 μm, preferably about 2 to about 5 μm. Preferably, the composition containing the compound with this particle size is in form of an ointment or cream, and when it is administered to the skin of a subject, greater than 90% of the compound (by number), preferably substantially all of the compound is retained in the skin for at least about 2 hours, more preferably about 4 hours, even more preferably about 6 hours, and most preferably about 8 hours after the administration. The retention rate and time of the compound in the skin can be measured through, for example, a diffusion cell study. In this study, a diffusion cell setup consisting essentially of a piece of skin clamped between two clamps is mounted, and a formulation containing the compound is applied on one side of the skin (top) and compound concentration is measured at certain time-intervals in a receiver portion (bottom) of the setup (which can be a container filled with buffer that is in contact with the skin).

Besides, when it is administered to the skin of a subject, the concentration of the compound can be, for example, about 8 to about 20 μg in per gram epidermis tissue, and/or about 1 to about 3 μg in per gram dermis tissue, after 8 hours from the administration.

In another embodiment, at least about 90% by volume of the compound in the composition has a particle size of about 10 to about 30 μm, preferably about 12 to about 25 μm. Preferably, the composition containing the compound with this particle size is in form of an ointment or cream, more preferably an ointment, and when it is administered to the skin of a subject, greater than 90% of the compound (by number), preferably substantially all of the compound is retained in the skin for at least preferably about 4 hours, more preferably about 6 hours, and most preferably about 8 hours after the administration.

Besides, when it is administered to the skin of a subject, the concentration of the compound can be, for example, about 3 to about 6 μg in per gram epidermis tissue, and/or about 0.2 to about 2 μg in per gram dermis tissue, after 8 hours from the administration.

The topical pharmaceutical composition having the above properties provides good balance between penetration and retention, and thus is useful in treatment of skin diseases, such as inflammatory and/or hyperpoliferative and pruritic skin diseases selected from atopic dermatitis, psoriasis, pustular psoriasis, rosacea, keloids, hypertrophic scars, acne, Netherton's syndrome or other pruritic dermatoses including prurigo nodularis, unspecified itch of the elderly, and diseases with epithelial barrier dysfunction including aged skin, and epidermolysis bullosa. Preferably, it is useful in treatment of epidermolysis bullosa.

The present invention also relates to a method of treating inflammatory and/or hyperpoliferative and pruritic skin diseases, and diseases with epithelial barrier dysfunction including aged skin and epidermolysis bullosa, comprising administering to a subject in need thereof an effective amount of the composition of the present invention.

The present invention further provides a topical diacerein/rhein pharmaceutical composition useful in treatment of hyperuricemia, a disorder associated with hyperuricemia (e.g., acute gout, chronic gout, gout flares, uric acid nephrolithiasis, gouty nephropathy, etc.), osteoarthritis and type 2 diabetes mellitus. In difference with those compositions used for treatment of skin diseases, the composition herein allows the active compound to penetrate easily into the skin and enter into the body relatively quicker, so as to reach systemic circulation and exert its function in the body. The topical composition comprises a therapeutically effective amount of a compound selected from the group consisting of diacerein, rhein, monoacetylrhein, and salts or esters or prodrugs thereof, and one or more pharmaceutically acceptable excipients, wherein the composition is in the form of gel, and at least about 90% by volume of the compound has a particle size of less than about 1 μm, and preferably greater than about 0.1 um.

Preferably, when the composition is administered to the skin of a subject, the compound is released from the skin into the body within about 6 hours, more preferably about 4 hours, and most preferably about 2 hours after the administration.

The present invention also provides a method of treating hyperuricemia, a disorder associated with hyperuricemia (e.g., acute gout, chronic gout, gout flares, uric acid nephrolithiasis, gouty nephropathy, etc.), osteoarthritis and type 2 diabetes mellitus, comprising administering to a subject in need thereof an effective amount of the composition of the present invention.

In some embodiments, the treatment methods of the invention specifically exclude administration of any other active agents to treat the diseases treatable by the compositions of the present invention. In some embodiments, however, the methods allow for administration of other active agents.

Preferably, the treatment methods of the invention result in effective treatment of the relevant disease in at least one treated subject, and preferably, in the substantial number of the treated subjects, and more preferably, in the majority of the treated subjects.

The topical pharmaceutical composition of the present invention may comprise preferably about 0.1% to about 10% w/w, more preferably about 0.1% to 5%, and most preferably about 0.5% to about 2% w/w of the compound based on the total weight of the composition.

The pharmaceutically acceptable excipients in the composition may include antioxidants, gelling agents/hydrogel bases, pH adjusting agents/buffers, penetration enhancers, preservatives, chelating agents, humectants, surfactants, emulsifiers, thickeners, solvents, stabilizers, etc. Herein, excipients/ingredients in the present invention may have multiple functions, e.g., one excipient can be used as surfactant and/or stabilizer and/or emulsifier, etc.

Examples of antioxidants include, but not limited to, one or more of vitamin C, vitamin A and alpha-lipoic acid, ascorbyl palmitate, sodium pyrosulfite, butyl hydroxy anisole (BHA), butyl hydroxy toluene (BHT), and the like.

Suitable gelling agents/hydrogel base may include, but not limited to, one or more of guar, xanthan, and carregeenan gums, anionic, nonionic, cationic and lipophilically modified guar gums, polyacrylic acids (e.g., carbomer), polymethacrylic acids, cellulose resins, polyethylene glycols, hydroxy alkyl celluloses, carboxy alkyl celluloses, polyalkylene amines, and the like.

Examples of pH adjusting agents/buffers include, but not limited to, one or more of sodium bicarbonate, potassium bicarbonate, magnesium hydroxide, magnesium lactate, magnesium gluconate, aluminum hydroxide, aluminum hydroxide/sodium bicarbonate co precipitate, amino acids, aluminum glycinate, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, sodium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, citric acid, and the like.

Examples of penetration enhancers includes, but not limited to, one or more of diethylene glycol monoethyl ether, dimethyl sulfoxide, propylene glycol, isopropyl myristate (IPM), cal-cipotriene, detergents, emollients, Ethoxy diglycol, Triacetin, Propylene Glycol, Benzyl Alcohol, Sodium Laureth Sulfate, Dimethyl Isosorbide, Isopropyl Myristate, Medium Chain Triglyceride Oil (MCT Oil), Menthol, Isopropyl Palmitate, Isopropyl Isostearate, Propylene Glycol Monostearate, Lecithin, Diisopropyl Adipate, Diethyl Sebacate, Oleic Acid, Ethyl Oleate, Urea, Glyceryl Oleate, Caprylic/Capric Triglyceride, Propylene Glycol Dicaprylate/Dicaprate, Laureth 4, Oleth-2, Oleth-20, Propylene Carbonate, Nonoxynol-9, 2-n-nonyl-1,3-dioxolane, C7 to C14-hydrocarbyl substituted 1,3-dioxolane, 1,3-dioxane, or acetal, and Nonoxynol-15, and the like.

Preservatives can be, for instance, one or more of sodium benzoate, butylated hydroxy toluene, butylated hydroxyanisole, ethylenediamine tetraacetic acid (EDTA), paraoxybenzoic acid esters, chlorobutanol, benzyl alcohol, phenylethyl alcohol, dehydroacetic acid, sorbic acid, benzalkonium chloride, benzethonium chloride, phenol, phenylmercuric nitrate, thimerosal, methyl-, ethyl-, and/or propyl-paraben.

Examples of suitable solvents include, but not limited to, one or more of alcohol, castor oil, diisopropyl adipate, ethoxylated alcohol, ethyl alcohol, fatty alcohol citrate, glycerin, 1,2,6-hexanetriol, hexylene glycol, isopropyl alcohol, isopropyl myristate, isopropyl palmitate, mineral oil, phosphoric acid, polyethylene glycol 300, polyethylene glycol 400, polyethylene glycol 1450, polyethylene glycol 8000, polyethylene glycol 1000 monocetyl ether, polyethylene glycol monostearate, polyethylene glycol 400 monostearate, polyethylene glycols, polyoxyl 20 cetostearyl ether, polyoxypropylene 15-stearyl ether, polysorbate 20, polysorbate 40, polysorbate 60, polysorbate 80, polysorbates, propylene carbonate, propylene glycol, purified water, SD alcohol 40, triglycerides of saturated fatty acids, and the like.

Suitable stabilizers or surfactants can be, for example, one or more of ionic polysorbate surfactant, Tween 20, Tween 40, Tween 60, Tween 80, nonylphenol polyethylene glycol ethers, (alkylphenol-hydroxypolyoxyethylene), Poly(oxy-1,2-ethanediyl), alpha-(4-nonylphenol)-omega-hydroxy-, branched (i.e., Tergitol® NP-40 Surfactant), nonylphenol polyethylene glycol ether mixtures (i.e., Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate, cetyl alcohol, stearic acid, polyoxyl stearate, and the like.

Examples of chelating agents include, but not limited to, antioxidants, citric acid, disodium edetate (EDTA), edetate calcium disodium, edetic acid, malic acid, maltol, pentetic acid, sodium edetate, trisodium edetate, and the like.

Examples of humectants include, but not limited to, glycerine, propylene glycol, sorbitol, polyethylene glycol, polysaccharides (such as fructose, glucose, maltose, etc.), corn syrup, polyols, urea and derivatives and natural honey. Preferred humectants are propylene glycol and glycerine.

Examples of thickeners include, but not limited to, stearic acid, cellulose polymer, a carbomer polymer, a carbomer derivative, a cellulose derivative, polyvinyl alcohol, poloxamers, polysaccharides, and the like.

Examples of oil base for cream include, but not limited to, vegetable oils (e.g., castor oil), white petrolatum, mineral oil, and the like.

Examples of ointment base include, but not limited to, petrolatum, fatty oil, lanolin, Vaseline, glycerine, paraffin, poloxamer, polyethylene glycol, stearic acid, bee wax, and the like. Examples of ointment base modifiers include, but not limited to, mineral oil, liquid paraffin, and the like.

In one embodiment, the topical pharmaceutical composition of the present invention is in form of a gel, and comprises about 0.1% to about 10% w/w of diacerein or its analogs, about 0.1% to about 5% w/w of a hydrogel base, about 2% to about 50% w/w of a humectant, and about 0.1% to about 2.5% w/w of a stabilizer/surfactant.

In one embodiment, the topical pharmaceutical composition of the present invention is in form of a cream, and comprises about 0.1% to about 10% w/w of diacerein or its analogs, about 0.5% to about 25% w/w of a surfactant, about 0.5 to about 25% w/w of an oil base, about 2% to about 50% w/w of a humectant, and water.

In one embodiment, the topical pharmaceutical composition of the present invention is in form of a cream, and comprises a part A and a part B; wherein the part A comprises about 0.1% to about 10% w/w of diacerein or its analogs, about 1.5% to about 40% w/w of a thickener, about 1% to about 40% of an oil base, and about 0.4% to about 10% w/w of a surfactant; and the part B comprises about 0.2% to about 5% w/w of a stabilizer, about 0.6% to about 15% w/w of a humectant, and water.

In one embodiment, the topical pharmaceutical composition of the present invention is in form of an ointment, and comprises 0.1% to about 10% w/w of diacerein or its analogs, about 15% to about 99% w/w of an ointment base, about 0% to about 60% w/w of a base modifier, and about 0% to about 10% w/w of a surfactant.

In one embodiment, the invention provides a topical pharmaceutical composition comprising a therapeutically effective amount of a compound selected from the group consisting of diacerein, rhein, monoacetylrhein, and salts or esters or prodrugs thereof, and one or more pharmaceutically acceptable excipients, wherein the composition is in the form of ointment, and at least about 90% by volume of the compound has a particle size of about 0.5 to about 35 µm.

In one embodiment, a composition is in the form of ointment and the pharmaceutically acceptable excipient comprises an ointment base, an ointment base modifier, and a surfactant.

In one embodiment, a composition is in the form of ointment and comprises about 0.1% to about 10% w/w of a compound selected from the group consisting of diacerein, rhein, monoacetylrhein, and salts or esters or prodrugs thereof; about 15% to about 99% w/w of an ointment base; about 0% to about 60% w/w of an ointment base modifier; and about 0% to about 10% w/w of a surfactant, based on the total weight of the composition; and wherein at least about 90% by volume of the compound has a particle size of about 0.5 to about 35 µm.

In one embodiment, a composition is in the form of ointment and comprises about 1% w/w of a compound selected from the group consisting of diacerein, rhein, monoacetylrhein, and salts or esters or prodrugs thereof; about 84.5% w/w of an ointment base, about 12% w/w of an ointment base modifier, and about 2% w/w of a surfactant, based on the total weight of the composition, and wherein at least about 90% by volume of the compound has a particle size of about 0.5 to about 35 µm.

In one embodiment, a composition is in the form of ointment and comprises about 0.1% to about 10% w/w of diacerein, about 15% to about 99% w/w of white petrolatum, about 0% to about 60% w/w of mineral oil, and about 0% to about 10% w/w of cetyl alcohol, based on the total weight of the composition, and wherein at least about 90% by volume of the compound has a particle size of about 0.5 to about 35 µm.

In one embodiment, a composition is in the form of ointment and comprises about 1% w/w of diacerein, about 84.5% w/w of white petrolatum, about 12% w/w of mineral oil, and about 2% w/w of cetyl alcohol, based on the total weight of the composition, and wherein at least about 90% by volume of the compound has a particle size of about 0.5 to about 35 µm.

Preferably, the topical pharmaceutical composition of the present invention is a once or twice-daily composition. That is, it is suitable to allow once or twice daily administration in order to achieve a desired therapeutic effect.

The topical pharmaceutical compositions of the present invention have the following advantages. First, they can be administered directly to the sites affected by dermatological subdermal conditions, bypassing the gastrointestinal route and having greatly reduced systemic exposure. Second, they are easy to apply and thus are more convenient for patients. Third, these topical formulations are also more preferred than oral ones for patients who suffer from dysphagia or are averse to the taste of the medicine. Fourth, they are easier to achieve sustained exposure to the targeted sites.

The present invention also relates to a method of treating inflammatory and/or hyperpoliferative and pruritic skin diseases, and diseases with epithelial barrier dysfunction including aged skin and epidermolysis bullosa, comprising administering to a subject in need thereof an effective amount of a topical pharmaceutical composition, wherein the composition comprises a therapeutically effective amount of a compound selected from the group consisting of diacerein, rhein, monoacetylrhein, and salts or esters or prodrugs thereof, and one or more pharmaceutically acceptable excipients; wherein when the composition is administered to the skin of the subject, greater than 90% (by number) of the compound is retained in the skin for at least about 2 hours, preferably at least about 4 hours, even more preferably about 6 hours, and most preferably about 8 hours after administration.

The present invention also relates to a method of treating inflammatory and/or hyperpoliferative and pruritic skin diseases, and diseases with epithelial barrier dysfunction including aged skin and epidermolysis bullosa, comprising administering to a subject in need thereof an effective amount of a topical pharmaceutical composition, wherein the composition comprises a therapeutically effective amount of a compound selected from the group consisting of diacerein, rhein, monoacetylrhein, and salts or esters or prodrugs thereof, and one or more pharmaceutically acceptable excipients; wherein when the composition is administered to the skin of the subject, the concentration of the compound can be, for example, about 8 to about 20 μg in per gram epidermis tissue, and/or about 1 to about 3 μg in per gram dermis tissue, after 8 hours from administration.

The present invention also relates to a method of treating inflammatory and/or hyperpoliferative and pruritic skin diseases, and diseases with epithelial barrier dysfunction including aged skin and epidermolysis bullosa, comprising administering to a subject in need thereof an effective amount of a topical pharmaceutical composition, wherein the composition comprises a therapeutically effective amount of a compound selected from the group consisting of diacerein, rhein, monoacetylrhein, and salts or esters or prodrugs thereof, and one or more pharmaceutically acceptable excipients; wherein when the composition is administered to the skin of the subject, the concentration of the compound can be, for example, about 3 to about 6 μg in per gram epidermis tissue, and/or about 0.2 to about 2 μg per gram dermis tissue, after 8 hours from administration.

The present invention further relates to a method of treating hyperuricemia, a disorder associated with hyperuricemia, osteoarthritis and type 2 diabetes mellitus, comprising administering to a subject in need thereof an effective amount of a topical pharmaceutical composition, wherein the composition comprises a therapeutically effective amount of a compound selected from the group consisting of diacerein, rhein, monoacetylrhein, and salts or esters or prodrugs thereof, and one or more pharmaceutically acceptable excipients; wherein when the composition is administered to the skin of the subject, the compound is released from the skin into the body within about 6 hours, more preferably about 4 hours, and most preferably about 2 hours after administration.

Hereinafter, the present invention will be further illustrated with reference to the following examples. However, these examples are only provided for illustrative purposes, but not to limit the scope of the present invention.

PREPARATION EXAMPLE

Preparation Of Diacerein Topical Compositions

Seven diacerein topical compositions (G1, C1, C2, and O1 to O4) with three different forms (gel, cream and ointment) were prepared according to following Tables 1 to 4. The particle size (Dv90) of the compound in each composition was measured by Mastersizer 2000 Ver. 5.60. Excipients/ingredients listed in the following tables may have multiple functions, e.g., one excipient is used as surfactant and/or stabilizer and/or emulsifier, etc.

TABLE 1

| | Gel | |
|---|---|---|
| | Formulation | |
| Ingredients (function) | Gx (Preferred Range) % (w/w) | G1 % (w/w) |
| Micronized Diacerein (active ingredient) | 0.1 to 10 | 1.00 |
| Carbomer (hydrogel base) | 0.1 to 5 | 1.00 |
| Methylparaben (preservative) | 0.01 to 0.25 | 0.10 |

TABLE 1-continued

| | Gel | |
|---|---|---|
| | Formulation | |
| Ingredients (function) | Gx (Preferred Range) % (w/w) | G1 % (w/w) |
| Propylparaben (preservative) | | 0.02 |
| EDTA (chelating agent) | 0.004 to 0.1 | 0.02 |
| Glycerin (humectant) | 2 to 50 | 10.00 |
| Tween 80 (stabilizer/surfactant) | 0.1 to 2.5 | 0.50 |
| Citric acid monohydrate (pH adjusting agents/buffers) | 0.025 to 0.7 | 0.13 |
| Sodium citrate dihydrate (pH adjusting agents/buffers) | | 0.14 |
| Total | 100.00 | 100.00 |

TABLE 2

| | Cream | |
|---|---|---|
| | Formulation | |
| Ingredients (function) | Cx (Preferred Range) % (w/w) | C1 % (w/w) |
| Part A | | |
| Micronized Diacerein (active ingredient) | 0.1 to 10 | 1 |
| Stearic acid (thickener) | 1.5 to 40 | 7.5 |
| Castor oil (oil base) | 1 to 40 | 8 |
| White petrolatum (oil base) | | 6 |
| SPAN 60 (surfactant) | 0.4 to 10 | 2 |
| Part B | | |
| Tween 60 (stabilizer) | 0.2 to 5 | 1 |
| EDTA (chelating agent) | 0.004 to 0.1 | 0.02 |
| Glycerin (humectant) | 0.6 to 15 | 3 |
| Methylparaben (preservative) | 0.01 to 0.25 | 0.1 |
| Propylparaben (preservative) | | 0.02 |
| Citric acid monohydrate (pH adjusting agents/buffers) | 0.025 to 0.7 | 0.13 |
| Sodium citrate dihydrate (pH adjusting agents/buffers) | | 0.14 |
| Purified water | q.s. | q.s. 100 |
| Diacerein Particle Size (Dv90, before mixed with other excipients) | 0.5 to 35 μm | 2.66 μm |

TABLE 3

Cream

| Ingredients | Cy (Preferred Range) % (w/w) | C2 % (w/w) |
|---|---|---|
| Micronized Diacerein (active ingredient) | 0.1 to 10 | 1 |
| Stearic acid (surfactant) | 0.5 to 25 | 9.75 |
| cetyl alcohol (surfactant) | | 3.25 |
| Polyoxyl 40 stearate (surfactant) | | 5 |
| Mineral oil (oil base) | 0.5 to 25 | 2.6 |
| Ethylparaben (preservative) | 0.1 to 2.5 | 0.5 |
| Purified water | q.s. | 67.7 |
| Propylene Glycerol (humectant) | 2 to 50 | 10.2 |
| Total | 100 | 100 |
| Diacerein Particle Size (Dv90, before mixed with other excipients) | 0.5 to 35 μm | 2.66 μm |

TABLE 4

Ointment

| Ingredients (function) | Ox (Preferred Range) % (w/w) | O1 % (w/w) | O2 % (w/w) | O3 % (w/w) | O4 % (w/w) |
|---|---|---|---|---|---|
| Micronized Diacerein (active ingredient) | 0 to 10 | — | 1.00 | — | 1.00 |
| Diacerein (active ingredient) | 0 to 10 | 1.00 | — | 1.00 | — |
| White Petrolatum (ointment base) | 15 to 99 | 74.00 | 82.00 | 82.00 | 84.5 |
| Mineral oil (ointment base modifier) | 0 to 60 | 25.00 | 16.00 | 16.00 | 12.00 |
| Cetyl Alcohol (surfactant) | 0 to 10 | — | 0.50 | 0.50 | 2.00 |
| Ethylparaben (preservative) | 0 to 2.5 | — | 0.50 | 0.50 | 0.50 |
| Total | 100.00 | 100.00 | 100.00 | 100.00 | 100.00 |
| Diacerein Particle size (Dv90) | 0.5 to 35 μm | N/A | Before mixing: 2.66 μm After mixing: 4.2 μm | Before mixing: 14.15 μm After mixing: 20 μm | N/A |

Example 1

Diffusion Cell Study of Topical Diacerein Compositions

Procedure: Mice were sacrificed by cervical dislocation. The full-thickness flank skin was removed and placed on the diffusion cell in contact with receptor phase, which was PBS (pH 5.4) with 30% PEG 300 (at 37° C.). Buffer was pumped through the receiver compartment at a flow rate of 3 to 4 mL/h. A dose of 20 μl of 1% diacerein gel (Formulation G1), 1% diacerein cream (Formulations C1 and C2), or 1% diacerein ointment (Formulations O1, O2 and O3) were added onto the skin surface in the donor compartment. Receiver solutions were collected at hours 0, 1, 2, 4, 6 and 8. At the end of 8 hours of treatment with the formulations, skin was dismounted from the diffusion cell, and the skin surface was cleaned carefully with three alcohol swabs (without tape-stripping). Epidermis was separated from dermis using scalpel blade. Both the separated epidermis and dermis were weighed and minced, and extracted twice with 0.5 ml acetonitrile:acetic acid:water (60:0.1:40) by vigorous shaking for 1 hour. The skin extracts were then centrifuged at 14,500 rpm for 20 minutes. All procedures were performed under reduced light. Both skin extracts and receiver solutions were stored at −20° C. until submitted for analyses of diacerein and rhein concentrations by HPLC (diacerein is easily converted into rhein during the experiment). Skin flux was calculated from the slope of the linear part of the cumulative penetration of rhein concentration versus time curve. The results are summarized as follows.

[The Influence of Forms on Penetrability and Retention]

Penetrability

As shown in FIG. 1, the gel diacerein formulation (G1) penetrates the stratum corneum better than the cream and ointment formulations (C1 and O1). After 8 hours from administration, rhein concentration in per gram epidermis is 204.0 μg for G1, 16.1 μg for C1, and 31.2 μg for O1; and rhein concentration in per gram dermis is 11.9 μg for G1, 2.53 μg for C1, and 3.14 μg for O1.

Retention

Figure 2A:
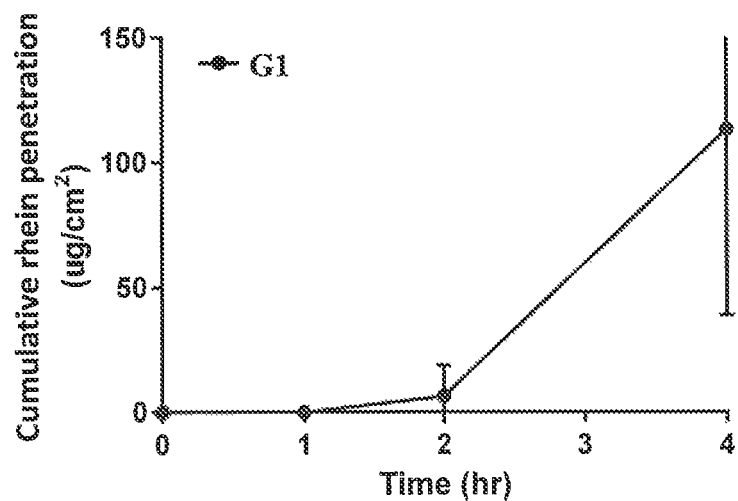
FIGS. 2A and 2B is a plot of cumulative rhein penetration (ng/cm$^2$) from the skin tissue into the receiver solution vs time for three tested diacerein formulations (G1, C1, and O1, n=4)
Figure 2B:
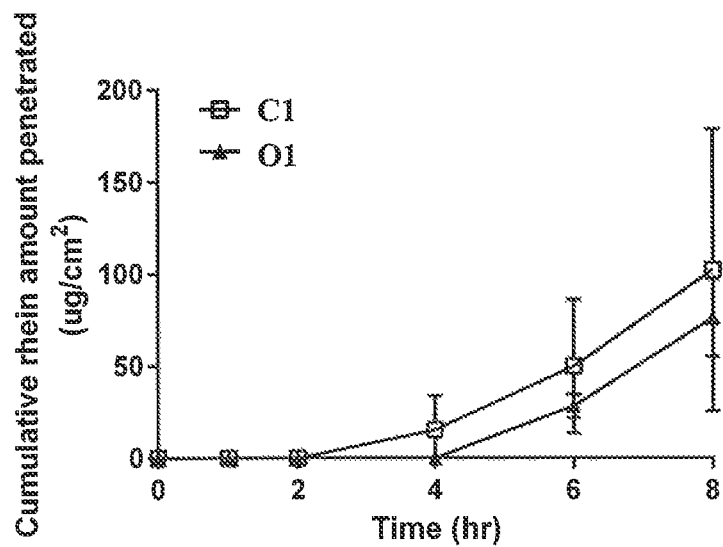

As shown in FIGS. 2A and 2B, rhein penetrated the skin tissue and was released into the receiver solution after 1 hour for the gel formulation (G1) and after 2 hours for the cream formulation (C1), but for the ointment formulation (O1), rhein did not penetrate the skin tissue and enter into the receiver solution until 4 hours, indicating that an ointment formulation has higher retention rate and longer retention time than gel and cream formulations.

The results indicate that diacerein/rhein would have a higher penetrability to the stratum corneum in a gel formulation as compared with a cream or ointment formulation, and would have a longer retention time in the skin target site in an ointment formulation as compared with a cream or gel formulation. The gel formulation has the shortest retention time in the skin target site among the three formulations.

[The Influence of Particle Size on Penetrability and Retention]

Figure 3:
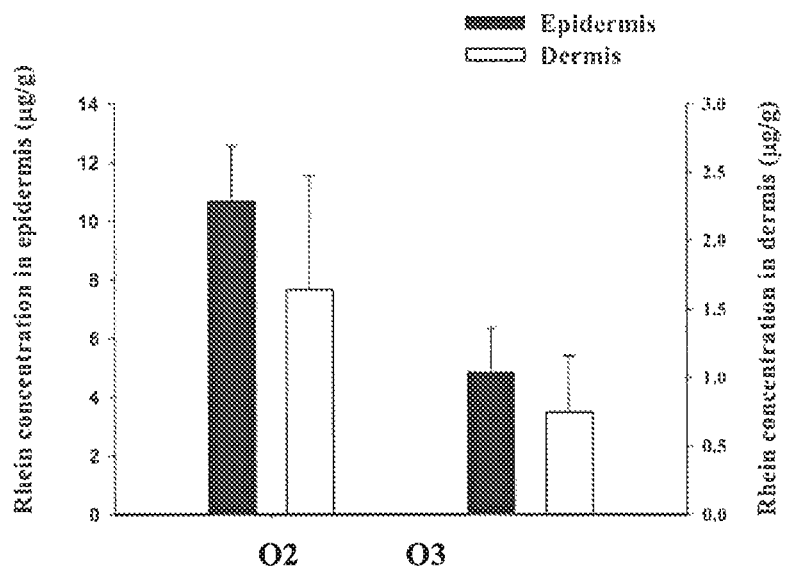
FIG. 3 is a statistical bar graph showing rhein concentrations in dermis and epidermis 8 hours post treatment with two tested diacerein ointment formulations (O2 and O3, n=3)

FIG. 3 shows that the ointment formulation having smaller particle size (O2) penetrated faster than that having larger particle size (O3). After 8 hours from administration, rhein concentration in per gram epidermis is 10.7 µg for O2, and 4.8 µg for O3; and rhein concentration in per gram dermis is 1.6 µg for O2, and 0.7 µg for O3.

Figure 4:
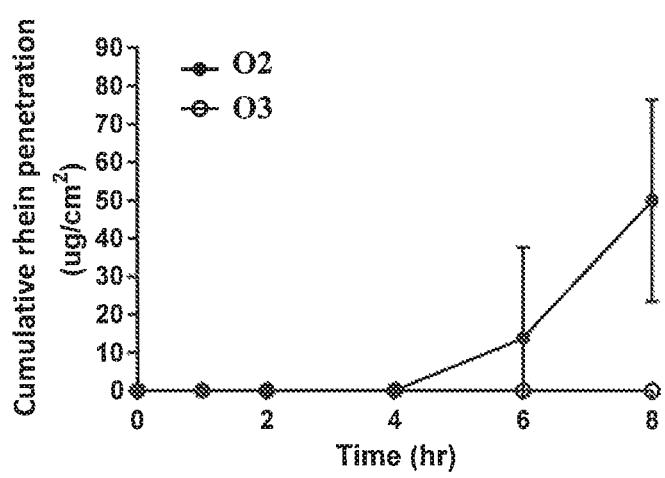
FIG. 4 is a plot of cumulative rhein penetration (ng/cm$^2$) from the skin tissue into the receiver solution vs time for two tested diacerein ointment formulations (O2 and O3, n=3)

FIG. 4 shows that the ointment formulation O2 released rhein after 4 hours, and the ointment formulation O3 did not release rhein until 8 hours or even longer. Ointment formulation O3 demonstrated similar compound concentration in skin layer, but has longer retention time compared to O2.

Example 2

Comparative Example

Wally et al. discloses a cream formulation containing 1% diacerein in a commonly used care cream Ultraphil® (Wally et al., Orphanet Journal of Rare Diseases, 2013, vol. 8, issue 69). A comparison study was conducted between this cream formulation (the comparative formulation) and the ointment formulation O3 of the present invention. The results are shown in FIGS. 5 and 6.

Figure 5:
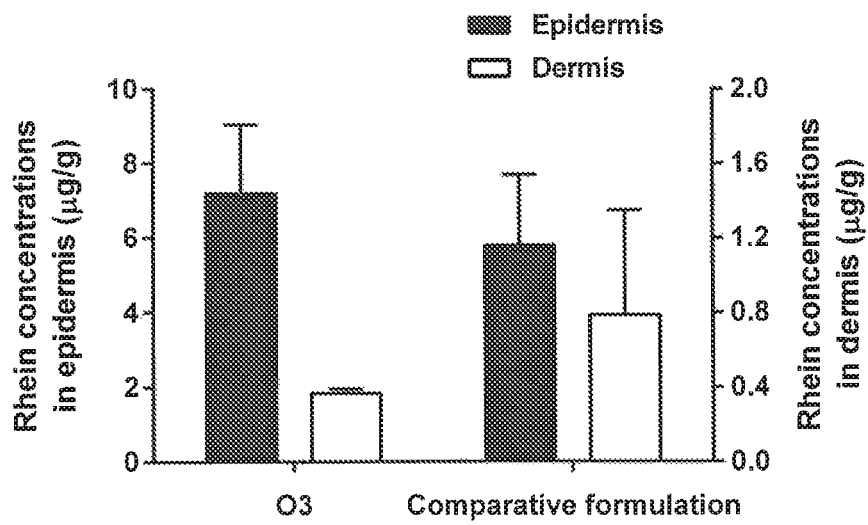
FIG. 5 is a statistical bar graph showing rhein concentrations in dermis and epidermis 8 hours post treatment with the tested diacerein ointment formulation (O3, n=3) or a comparative formulation (n=3)
Figure 6:
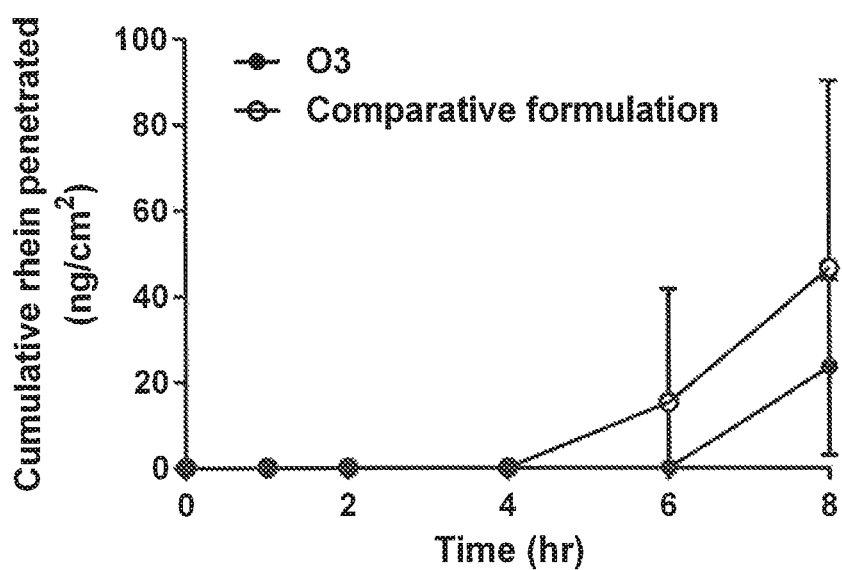
FIG. 6 is a plot of cumulative rhein penetration (ng/cm$^2$) from the skin tissue into the receiver solution vs time for the tested diacerein ointment formulation (O3, n=3) and the comparative formulation (n=3).

As shown in FIG. 5, the ointment formulation O3 penetrated the stratum corneum more than the comparative formulation and reveals higher retention in the skin layer. Furthermore, as shown in FIG. 6, rhein in the comparative formulation penetrated the skin tissue and was detectable in the receiver solution after 4 hours, but rhein in the O3 formulation did not penetrate the skin tissue into the receiver solution until 6 hours.

The results demonstrated that the O3 formulation has a higher penetrability to the stratum corneum, a higher retention rate, and longer retention duration than the comparative formulation, indicating a higher drug concentration maintained in the skin layer with the O3 formulation.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A topical pharmaceutical composition comprising a therapeutically effective amount of a compound selected from the group consisting of diacerein, rhein, monoacetyl-rhein, and salts or esters or prodrugs thereof, and one or more pharmaceutically acceptable excipients, wherein the composition is in the form of an ointment, and at least about 90% by volume of the compound has a particle size of about 0.5 to about 35 µm, wherein the pharmaceutically acceptable excipient comprises an ointment base, an ointment base modifier, and a surfactant.

2. The composition of claim 1, wherein the compound is present in an amount between about 0.1% to about 10.0% w/w of the total composition.

3. The composition of claim 1, comprising about 0.1% to about 10% w/w of the compound, about 15% to about 99% w/w of an ointment base, about 0% to about 60% w/w of an ointment base modifier, and about 0% to about 10% w/w of a surfactant, based on the total weight of the composition.

4. A topical pharmaceutical composition comprising a therapeutically effective amount of a compound selected from the group consisting of diacerein, rhein, monoacetyl-rhein, and salts or esters or prodrugs thereof, and one or more pharmaceutically acceptable excipients, wherein the composition is in the form of an ointment, and at least about 90% by volume of the compound has a particle size of about 0.5 to about 35 µm, comprising about 0.1% to about 10% w/w of diacerein, about 15% to about 99% w/w of white petrolatum, about 0% to about 60% w/w of mineral oil, and about 0% to about 10% w/w of cetyl alcohol, based on the total weight of the composition.

5. The composition of claim 1 or 4, comprising about 1% w/w of diacerein, about 84.5% w/w of white petrolatum, about 12% w/w of mineral oil, and about 2% w/w of cetyl alcohol, based on the total weight of the composition.

6. The composition of claim 5, wherein at least about 90% by volume of the compound has a particle size of about 14 to about 20 pm.

7. The composition of claim 1 or 4, wherein when the composition is administered to the skin of a subject, greater than 90% (by number) of the compound is retained in the skin for at least about 2 hours after administration.

8. The composition of claim 1 or 4, which is a once or twice- daily composition.

9. A method of treating inflammatory and/or hyperproliferative and pruritic skin diseases, and diseases with epithelial barrier dysfunction, comprising administering to a subject in need thereof an effective amount of the composition of claim 1 or 4.

10. The method of claim 9, wherein the inflammatory and/or hyperpoliferative and pruritic skin diseases are selected from atopic dermatitis, psoriasis, pustular psoriasis, rosacea, keloids, hypertrophic scars, acne, Netherton's syndrome or other pruritic dermatoses including prurigo nodularis, unspecified itch of the elderly, diseases with epithelial barrier dysfunction including aged skin, and epidermolysis bullosa.

11. The method of claim 9, wherein the diseases with epithelial barrier dysfunction comprise aged skin and epidermolysis bullosa.

12. A method of treating epidermolysis bullosa, comprising administering to a subject in need thereof an effective amount of the composition of claim 6.

* * * * *